United States Patent
Cooper

(10) Patent No.: US 9,746,397 B2
(45) Date of Patent: Aug. 29, 2017

(54) SAMPLE FLUID STREAM PROBE GAS SHEET NOZZLE

(71) Applicant: Cooper Environmental Services LLC, Beaverton, OR (US)

(72) Inventor: John Arthur Cooper, Beaverton, OR (US)

(73) Assignee: Cooper Environmental Services LLC, Beaverton, OR (US)

( * ) Notice: Subject to any disclaimer, the term of this patent is extended or adjusted under 35 U.S.C. 154(b) by 33 days.

(21) Appl. No.: 14/803,615

(22) Filed: Jul. 20, 2015

(65) Prior Publication Data

US 2017/0023447 A1 Jan. 26, 2017

(51) Int. Cl.
*G01N 1/22* (2006.01)

(52) U.S. Cl.
CPC ... *G01N 1/2258* (2013.01); *G01N 2001/2267* (2013.01)

(58) Field of Classification Search
CPC ......... G01N 1/2035; G01N 2001/2064; G01N 1/2247; G01N 1/2258
USPC ....... 73/864, 863.41, 863.51, 863.61, 864.81
See application file for complete search history.

(56) References Cited

U.S. PATENT DOCUMENTS

| | | | |
|---|---|---|---|
| 2,987,921 A | 6/1961 | Kraftson et al. | |
| 4,060,001 A | 11/1977 | Archerd | |
| 4,653,334 A | 3/1987 | Capone | |
| 4,942,774 A | 7/1990 | McFarland | |
| 5,109,708 A | 5/1992 | Lawless | |
| 5,109,711 A | 5/1992 | Wendt | |
| 5,899,387 A * | 5/1999 | Haruch | B05B 7/0458 239/296 |
| 6,021,678 A | 2/2000 | Vardiman et al. | |
| 7,731,100 B2 | 6/2010 | Walsh, Jr. | |
| 8,028,934 B2 | 10/2011 | Wurz et al. | |
| 8,590,812 B2 | 11/2013 | Wurz | |
| 8,672,241 B2 | 3/2014 | Wurz | |
| 8,857,740 B2 | 10/2014 | Wurz | |
| 9,074,969 B2 | 7/2015 | Cooper | |
| 2002/0134174 A1 | 9/2002 | Silvis et al. | |
| 2002/0162335 A1 | 11/2002 | Steinthorsson et al. | |
| 2003/0133111 A1 | 7/2003 | Yamaguchi | |
| 2007/0169889 A1* | 7/2007 | Clark | B01D 53/38 156/345.29 |

(Continued)

OTHER PUBLICATIONS

"Nozzle", Accessed at: <<http://en.wikipedia.org/wiki/Nozzle>>, Accessed on Jan. 15, 2015, 4 Pages.
Haglund, et al., "A Continuous Emission Monitor for Quantitative Measurement of PM10 Emissions from Stationary Sources", For Presentation at the Air & Waste Management Association's 93rd Annual Conference & Exhibition, Jun. 18-22, 2000, 15 Pages.
Cain. et al., "Qualitative and Quantitative Wind Tunnel Measurements of the Airflow Through a Shrouded Airborne Aerosol Sampling Probe", 1998, pp. 1157-1169, J. Aerosol Sci. vol. 29, No. 9.
Gong, et al., "A Predictive Model for Aerosol Transmission Through a Shrouded Probe", 1996, pp. 3192-3198, Environ. Sci. Technol., vol. 30, No. 11.

(Continued)

*Primary Examiner* — Lisa Caputo
*Assistant Examiner* — Philip Cotey
(74) *Attorney, Agent, or Firm* — Jared S. Goff; Goff Patent Law PLLC

(57) ABSTRACT

A sample fluid stream can be received from a main fluid stream through a nozzle of a probe located at least partially in the main fluid stream. The sample fluid stream can travel into the nozzle and a portion of the main fluid stream adjacent to the sample fluid stream can flow past the probe without entering the probe. The sample fluid stream can flow downstream within the probe, and a portion of the main fluid stream can flow downstream outside the probe. While receiving the sample fluid stream, a gas sheet can be directed from the probe, with the gas sheet flowing upstream against the main fluid stream.

21 Claims, 3 Drawing Sheets

(56) References Cited

U.S. PATENT DOCUMENTS

| | | | |
|---|---|---|---|
| 2009/0120252 A1* | 5/2009 | Petrovich | B26D 1/085 83/53 |
| 2010/0116900 A1* | 5/2010 | Wurz | F23D 11/102 239/8 |
| 2010/0186523 A1* | 7/2010 | Vesala | G01N 1/2247 73/863.11 |
| 2011/0024334 A1* | 2/2011 | Althouse | B07B 4/02 209/139.1 |
| 2012/0255376 A1* | 10/2012 | Staymates | G01N 1/22 73/863.22 |
| 2013/0068852 A1 | 3/2013 | Wurz et al. | |
| 2013/0276904 A1* | 10/2013 | Cooper | G01N 1/2258 137/13 |
| 2014/0048615 A1 | 2/2014 | Wurz | |
| 2014/0290340 A1 | 10/2014 | Murthy et al. | |

OTHER PUBLICATIONS

Jimenez, et al., "A Comparative Study of Different Methods for the Sampling of High Temperature Combustion Aerosols", 2005, pp. 811-821, Aerosol Science and Technology, vol. 39.

Podgorski, et al., "Numerical Analysis of the Airflow Hydrodynamics Near the Inlet to a Shrouded Probe for Sampling of Atmospheric Aerosol Particles at High Velocities", 2000, pp. S412-S413, J. Aerosol Sci., vol. 31, Suppl. 1.

McFarland, et al., "Single-Point Representative Sampling with Shrouded Probes", Aug. 1993, pp. 1-26.

Rodgers, et al., "Representative Sampling and Monitoring of Airborne Radioactive Effluent at Los Alamos National Laboratory", Revised: Aug. 1993, 99 Pages.

\* cited by examiner

SAMPLE FLUID STREAM PROBE GAS SHEET NOZZLE

BACKGROUND

Probes can be used to collect sample fluid streams from main fluid streams. For example, probes can be used to collect sample fluid streams from stack emissions, such as wet stack emissions. Wet stacks are stacks containing main flows of emissions that are saturated with water vapor and have liquid water droplets that can vary from micro droplets typical of fogs (micrometers in diameter) to macro droplets typical of rain (millimeters in diameter). These droplets can contain a large fraction of particulate matter (PM) and metals associated with health effects. It can be difficult to collect a representative sample of these droplets for analysis on a continuous basis. Currently, continuous emission monitor systems (CEMS) use large diameter probes to reduce deviations from isokinetic sampling, avoid heating sampling probes to minimize dried salt plugs, use steam and compressed air "blow back" to prevent probe build up and plugging, or other similar techniques to allow continuous operations.

SUMMARY

Current probes can be ineffective in transporting a representative total stack aerosol sample to a CEMS. The description herein is directed to tools and techniques for probe apparatuses for collecting and transporting sample fluid streams.

For example, a sample fluid stream can be received from a main fluid stream through a nozzle of a probe located at least partially in the main fluid stream. The sample fluid stream can travel into the nozzle and a portion of the main fluid stream adjacent to the sample fluid stream can flow past the probe without entering the probe. The sample fluid stream can flow downstream within the probe, and a portion of the main fluid stream can flow downstream outside the probe. While receiving the sample fluid stream, a gas sheet can be directed from the probe, with the gas sheet flowing upstream against the main fluid stream. As used herein downstream or a downstream direction refers to the direction of flow of the main fluid stream or sample fluid stream in an area at or adjacent to a specified feature, while an upstream direction refers to a direction of a flow that goes against such downstream flow direction.

This Summary is provided to introduce a selection of concepts in a simplified form. The concepts are further described below in the Detailed Description. This Summary is not intended to identify key features or essential features of the claimed subject matter, nor is it intended to be used to limit the scope of the claimed subject matter. Similarly, the invention is not limited to implementations that address the particular techniques, tools, environments, disadvantages, or advantages discussed in the Background, the Detailed Description, or the attached drawings.

BRIEF DESCRIPTION OF THE DRAWINGS

The description and drawings may refer to the same or similar features in different drawings with the same reference numbers.

DETAILED DESCRIPTION

Figure 1:
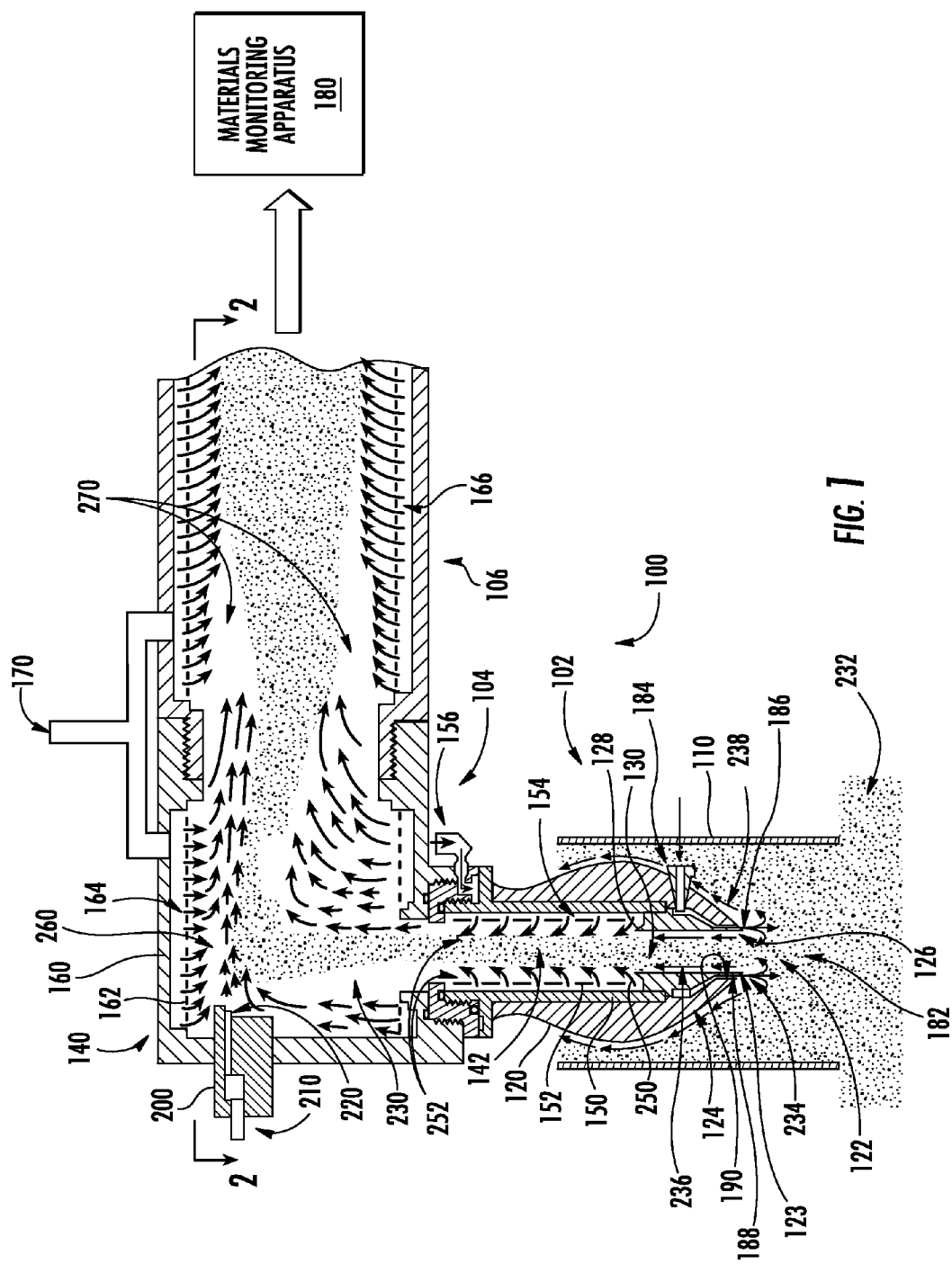
FIG. 1 is a side sectional view of a probe apparatus and taken along line 1-1 in FIG. 2, with a materials monitoring apparatus illustrated schematically.

Droplets from sample flow entering a sampling probe can deposit on the nozzle, run down the inside wall of the nozzle and dry to a salt deposit before being re-aerosolized into the flow. The same thing may occur from main flow passing by the nozzle and collecting on external surfaces of the nozzle and other surfaces of the probe. One or more of the virtual nozzle features can inhibit the collection of such droplets and materials contained in such droplets on the internal and/or external surfaces of the probe. The gas sheet virtual nozzle features discussed herein, wherein a gas sheet forms a virtual nozzle upstream of the actual nozzle, can help keep both the inside and outside surfaces of the nozzle clean, and may allow for a shorter nozzle to work effectively.

The probe features discussed herein include a gas sheet that is directed upstream of a leading portion of the probe nozzle against a downstream-flowing main fluid stream while the probe is receiving a sample fluid stream from the main fluid stream. The gas sheet can separate the sample fluid stream from the main fluid stream upstream of a leading edge of the probe. Moreover, gas from the gas sheet can form boundary layers of gas that can inhibit collection of material from the fluid streams on surfaces of the probe, such as the leading edge of the probe nozzle, inner surface(s) of the probe (that face inwardly toward the sample fluid stream in the probe), and outer surface(s) of the probe (that face outwardly toward a portion of the main fluid stream that is passing around the probe).

The inlet of the probe (nozzle and associated parts) can include features related to a virtual nozzle using a circular air knife as the nozzle inlet. As used herein, an air knife produces a high velocity thin gas sheet. The gas sheet of the nozzle may be included with one or more other probe features. For example, the probe apparatus can use high velocity gas to redirect the flow of stack gas, particles and liquid droplets from the original direction of the stack gas to a direction towards the containment walls, where the aerosol can be sampled or analyzed. For example, the high velocity gas can be in the form of a gas sheet, which can have a width that is at least ten times, at least fifty times, at least one-hundred times, at least five-hundred times, or at least one-thousand times a thickness of the gas sheet at an outlet of a gas knife. Other features can relate to reducing impaction of aerosol components in the sample fluid stream on conduit walls, encouraging re-entrainment of liquid deposited on walls of the inlet nozzle, etc. Alternatively, the gas sheet nozzle may be included in a probe without any of these other features.

The virtual nozzle features discussed herein may produce one or more of various benefits. For example, the virtual nozzle features may do one or more of the following: (1) keep the inside and/or outside of the nozzle clean because clean air from the gas sheet of the virtual nozzle will be flowing over these surfaces in a boundary layer; (2) if super isokinetic sampling conditions are used, this nozzle can be less likely to enrich fine particles than would be the case when using a standard nozzle; (3) begin the drying process by diluting the incoming stack gas with dry compressed air, which can break up droplets that would otherwise hit the nozzle; (4) helping to focus the wet stack gas aerosol towards the center of the flow and away from the walls downstream, potentially minimizing the length of pipe to produce proper focusing of the sample flow prior to the second air knife in the redirection area.

Figure 2:
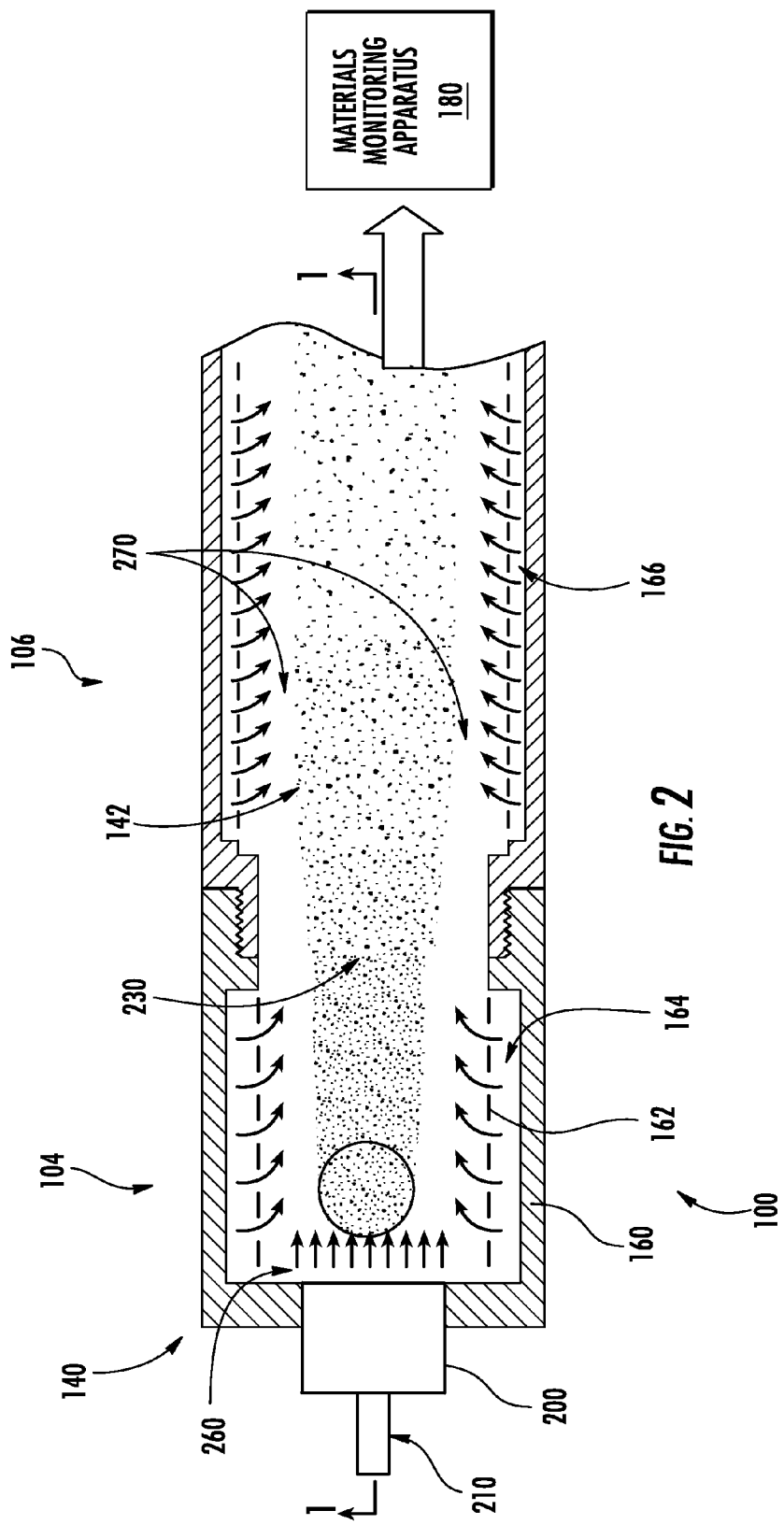
FIG. 2 is a top sectional of the probe apparatus of FIG. 1 taken along line 2-2 in FIG. 1, with the materials monitoring apparatus again illustrated schematically.

The various aspects of such features will now be discussed with reference to FIGS. 1-2. Referring to FIG. 1, a probe apparatus 100 is illustrated. The probe apparatus 100 can include a nozzle area 102, a redirection area 104 downstream of the nozzle area 102, and a transport area 106 downstream of the redirection area 104. For example, the nozzle area 102 may be oriented vertically, with the redirection area 104 turning ninety degrees, and the transport area 106 extending horizontally from the redirection area 104. The nozzle area 102 can include a shroud 110, which can be mounted on a nozzle 120. The shroud 110 can be a tube that is connected to the nozzle 120 with circumferentially spaced beams (not shown) extending between the nozzle 120 and the shroud 110 to mount the shroud on the nozzle.

The nozzle 120 can have a nozzle inlet 122 defined by a leading edge 123 of the nozzle 120. The nozzle inlet 122 can be centrally located within the shroud 110. The nozzle inlet 122 can have a diameter that is substantially smaller than an inner diameter of an entrance to the shroud 110 (e.g., from 0.1 to 0.4 times the diameter of the shroud 110). For example, the nozzle inlet may have a diameter of about three-fourths of an inch and the shroud may have an inner diameter of about three inches. The nozzle can have an outer surface 124 that can slope outward downstream of the inlet 122. An inner surface 126 of the nozzle 120 can extend downstream from the nozzle inlet 122. The inner surface 126 can have a constant diameter for some length (e.g., for between 1/16 inch to 1/4 inch, or 1/8 inch), and can end in a lip 128. From the lip 128, the inner surface 126 can form a reverse taper 130. The reverse taper 130 can extend outward at any of various different angles, such as an angle less than ninety degrees and/or an angle greater than ninety degrees. Additionally, the inner surface 126 can form a reverse taper upstream of the lip 128, with the inner surface 126 sloping outward downstream of the inlet 122.

A main conduit 140 can extend back from the nozzle inlet 122, defining a stream area 142 where the sample fluid stream is to flow, as will be discussed more below. The main conduit 140 can include the nozzle 120 and the other conduit components discussed below (e.g., the outer non-porous and inner porous conduit components).

A downstream portion of the nozzle 120 can fit over at least a portion of a first outer non-porous conduit component 150 or can otherwise be secured to the non-porous conduit component 150. The first outer non-porous conduit component 150 can surround a first inner porous conduit component 152 to form a first annular gas chamber 154 between the components 150. A focusing gas source 156 can be connected in fluid communication with the first gas chamber 154. The first outer non-porous conduit component 150 can be sealed to the first inner porous conduit component 152. This seal may not be an entirely gas-tight seal, but it can be sealed sufficiently to force focusing gas to pass through the first inner porous conduit component 152. The focusing gas source 156 can provide focusing gas that is at a temperature at or below the temperature of the main fluid stream entering the nozzle 120.

Downstream of the nozzle area 102, the stream area 142 can continue and the main conduit 140 can include a second outer non-porous conduit component 160 surrounding a second inner porous conduit component 162 to form a second annular gas chamber 164 between the second outer non-porous conduit component 160 and the second inner porous conduit component 162. A drying gas source 170 can be connected in fluid communication with the second gas chamber 164. The second outer non-porous conduit component 160 can be sealed to the first inner porous conduit component 162. This seal may not be an entirely gas-tight seal, but it can be sealed sufficiently to force focusing gas to pass through the first inner porous conduit component 162. The focusing gas source 156 can provide focusing gas that is also heated to act as drying gas. Accordingly, the drying gas can be at a temperature that is above the temperature of the main fluid stream entering the nozzle 120. The second gas chamber 164 can extend along the redirection area 104 and along the transport area 106, providing drying gas through the second inner porous conduit component 162. The second gas chamber 164 may be interrupted by a joint in the main conduit 140, so that there is also a third gas chamber 166 that can also supply drying gas. There may also be additional gas chambers to supply drying gas and/or unheated focusing gas downstream of the third gas chamber 166, leading to a materials monitoring apparatus 180 shown schematically in FIGS. 1 and 2. The materials monitoring apparatus 180 may be any of various types that are able to test the nature and/or quantity of particles in the sample stream flowing through the probe apparatus 100. For example, the monitoring apparatus 180 may be an X-ray fluorescence testing apparatus.

The probe apparatus 100 can include a virtual nozzle 182, which can include a pressurized gas source 184 that is fluidly connected to a gas sheet outlet 186 to produce a high velocity sheet of gas flowing upstream of the actual nozzle 120. The gas sheet outlet 186 can be an annular opening defined by an inner surface 188 that faces outwardly toward an outer surface 190, to define the outlet 186 between the inner surface 188 and the outer surface 190. The inner surface 188 can extend farther upstream (relative to the direction of flow of fluid into the probe apparatus 100 through the nozzle 120). For example, the inner surface 188 can extend upstream to the leading edge 123 of the nozzle 120 (which may not be a sharp edge, but may be rounded or some other shape). In one example, the distance from the inner surface 188 to the outer surface 190 (which is also the thickness of the outlet 186) can be from one thousandth to three thousandths of an inch. In other examples, the thickness of the outlet 186 can be from half a thousandth of an inch to twenty thousandths of an inch, or the thickness of the outlet 186 can be more than twenty thousandths of an inch or less than half a thousandth of an inch.

Additionally, the probe apparatus 100 can include a redirecting gas knife 200 that can be connected to a pressurized gas source 210. The gas knife 200 can define a gap that acts as an outlet 220 through which the pressurized gas can be forced to form a high velocity sheet of flowing gas. The outlet 220 may be curved so that the gas sheet is also curved. For example, the outlet 220 can form a concave curve from the perspective of the nozzle 120. Accordingly, the curve of the outlet 220 may match the curve of the conduit 140 distal from the nozzle 120 in FIGS. 1-2. The curve may have a radius of curvature that is the same as a radius of the main conduit 140 in the redirection area 104, and the curve may extend through a radial arc of from forty-five to one-hundred and eighty degrees, such as from ninety degrees to one-hundred and twenty degrees. The outlet 220 can have a width that is greater than a diameter of the sample stream flowing into the redirection area 104, and the outlet 220 can have a thickness that is less than the width. For example, the outlet 220 can have can have a width that is at least ten times, at least fifty times, at least one-hundred times, at least five-hundred times, or at least one-thousand times a thickness of the outlet 220. For example, outlet 220 may be one and one-half inches wide, and one one-thousandth of an inch thick (from top to bottom). The outlet 220 of the gas knife 200 can be directed into the redirection area 104. The outlet 220 can be pointed in a different direction from the direction of the flow into the nozzle inlet 122 and into the redirection area 104. For example, the outlet 220 can be pointed in the same direction as the direction of the main conduit 140 downstream of the redirection area 104. If the conduit makes a ninety-degree turn so that the main conduit 140 downstream of the redirection area 104 is at a right angle to the nozzle 120, the outlet 220 of the gas knife 200 may also be directed at that same right angle.

Various different materials and/or manufacturing methods may be used in the components of the probe apparatus 100. For example, the components may be made of corrosive-resistant metals such as stainless steel, titanium, or aluminum. Additionally, lightweight metals such as aluminum may be coated with corrosive-resistant coatings. The inner porous conduit components (152 and 162) may be sintered material such as sintered stainless steel.

Figure 3:
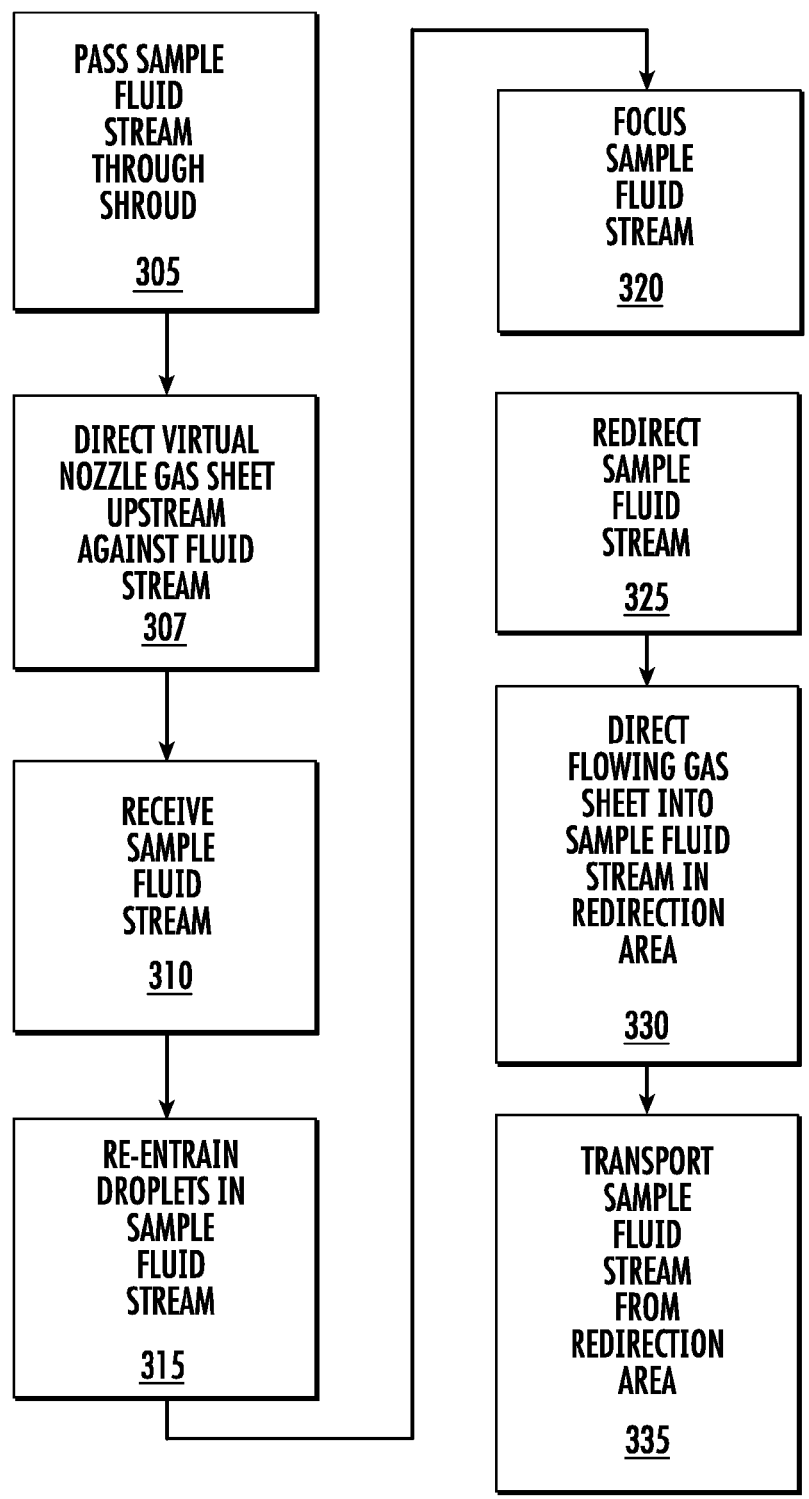
FIG. 3 is a flowchart illustrating a probe technique.

Operation of the probe apparatus 100 is discussed below with reference to a flowchart illustrated in FIG. 3, and still with—reference to FIGS. 1-2. A sample fluid stream 230 from a main fluid stream 232 can be passed 305 through the shroud 110 and then received 310 through the nozzle 120 of the probe apparatus 100, with the main fluid stream 232 and the sample fluid stream 230 both flowing in a downstream direction directly into and aligned with the nozzle inlet 122. The shroud 110 can slow the velocity of the fluid stream that passes through the shroud 110. This can create non-isokinetic flow around the edges of the shroud 110, which may cause a disproportionate number of particular sized particles to enter the shroud (e.g., disproportionately more large particles such as droplets). However, the flow around the edge of the shroud 110 can pass by the nozzle 120 without entering the nozzle inlet 122. The sample fluid stream 230 that enters the nozzle inlet 122 can be from the center of the shroud 110, where the non-isokinetic effects of the shroud can be reduced or non-existent. Additionally, the slowed velocity within the shroud 110 can reduce the non-isokinetic effects of the nozzle 120 on the sample fluid stream 230 entering the nozzle inlet 122. The slowed velocity can reduce the rate of capture of the sample fluid stream 230, so that there can be less flow to be transported and analyzed.

The sample fluid stream 230 can travel into the nozzle 120 in a first downstream direction. The virtual nozzle 182 can direct 307 a gas sheet 234 upstream against the flow of the main fluid stream 232 so that the gas sheet 234 separates the sample fluid stream 230 from the main fluid stream 232 within the shroud 110. Thus, the gas sheet 234 can separate the sample fluid stream 230 from the main fluid stream without the main fluid stream 232 or the sample fluid stream 230 needing to impact the leading edge 123 of the actual nozzle 120. The gas sheet outlet 186 can be configured so that the annular gas sheet 234 flows out of the outlet 186 against the incoming main fluid stream 232 and sample fluid stream 230, with the gas sheet 234 surrounding the sample fluid stream 234 as the sample fluid stream 230 flows to the nozzle inlet 122. For example, the annular gas sheet 234 can flow in a direction that is one-hundred eighty degrees relative to the downstream direction of the flow of the main fluid stream 232 and sample fluid stream 230 as those streams approach the nozzle 120. The flow direction of the gas sheet 234 may flow against the main fluid stream 232 and sample fluid stream 230 (so that it opposes the flow of those streams) without being directly opposed to those streams. For example, the gas sheet 234 may be within 0.5 degree, within 1 degree, within 2 degrees, or within 3 degrees of a direction that is 180 degrees from the flow direction of the main fluid stream 232 and sample fluid stream 230. If the gas sheet 234 is off too far from 180 degrees from the flow direction of the main fluid stream 232 and sample fluid stream 230, such a direction may cause a non-representative sampling of different droplet sizes from the main fluid stream 232 to enter the sample fluid stream 230. That non-representative sampling may be outside of allowable tolerances relative to a precisely accurate sampling of representative droplet sizes from the main fluid stream 232 in the sample fluid stream 230.

The velocity of the gas sheet 234 can be such that the gas sheet 234 can sheer and split at least some of the droplets in the main fluid stream 232. Also, the velocity of the gas sheet 234 can be high enough to inhibit impaction of droplets from the main fluid stream 232 and sample fluid stream 230 on the leading edge 123 of the nozzle 120. The main fluid stream 232 and the sample fluid stream 230 can slow the gas in the gas sheet 234 and can force gas from the gas sheet 234 back downstream. Thus, the gas sheet 234 can be blurred as it extends farther from the gas sheet outlet 186. However, force from the gas sheet 234 itself can inhibit movement of gas from the gas sheet 234 (and material in the main fluid stream 232 and sample fluid stream 230) directly back toward the gas sheet outlet 186. Accordingly, the gas sheet 234 can form a barrier to inhibit collection of material from the gas stream on the leading edge 123 of the nozzle 120.

Also, the configuration of flow of the gas sheet 234 can be such that gas from the gas sheet 234 that flows back downstream forms an internal boundary layer 236 flowing downstream adjacent to walls of the conduit 140 within the probe apparatus 100. This boundary layer 236 can focus the sample fluid stream 230 within a central portion of the conduit 140. Accordingly, the gas from the gas sheet 234 can inhibit collection of material from the sample fluid stream 230 onto the walls (e.g., onto the inner surface 126 of the nozzle 120) of the conduit 140. Additionally, the flow of the gas sheet 234 can be configured so that gas from the gas sheet 234 forms an external boundary layer 238 flowing downstream adjacent to external surfaces (e.g., the outer surface 124 of the nozzle 120) of the probe apparatus 100. Accordingly, the gas from the gas sheet 234 can also inhibit collection of material from the main fluid stream 232 on the external surfaces of the probe apparatus 100.

Some droplets (not shown) from the main fluid stream 232 that are not in the sample fluid stream 230 may still make it through the external boundary layer 238 and collect on the outer surface 124 of the nozzle 120. Other droplets (not shown) in the sample fluid stream 230 may make it through the internal boundary layer 236 to impact and collect on the inner surface 126 of the nozzle 120. Such droplets can be forced farther into the nozzle 120 by the flow of the sample fluid stream 230 and/or the flow of the internal boundary layer 236. These droplets can be re-entrained 315 in the sample fluid stream 230. For example, the droplets may collect on the lip 128 that is upstream of at least a portion of the reverse taper 130. A re-entraining gas flow 250 (e.g., part of a flow of focusing gas 252 from the first gas chamber 154) can be directed along a flow path to the droplets, such as by flowing along the lip 128 and carrying the droplets back into the sample fluid stream 230.

The focusing gas 252 passing through the first inner porous conduit component 152 can also be directed into the sample fluid stream 230 from multiple different sides (e.g., from all around the sample fluid stream 230 so that the focusing gas 252 surrounds the sample fluid stream 230) to focus 320 the sample fluid stream into a central area away from the surrounding walls of the first inner porous conduit component 152. This focusing 320 can reduce impaction of droplets and/or dry particles from the sample fluid stream 230 from impacting walls of the main conduit 140. Additionally, the reverse taper 130 brings the walls of the main conduit 140 out and away from the sample fluid stream 230, which can also reduce impaction of droplets and/or dry particles from the sample fluid stream 230 on walls of the main conduit 140.

The sample fluid stream 230 can be redirected 325 in the redirection area 104 from the first sample fluid stream direction to a second sample fluid stream direction. A flowing gas sheet 260 can be directed 330 into the sample fluid stream 230 in the redirection area 104, such as through the gas knife 200. The gas sheet 260 can be traveling in a sheet direction that is different from the first sample fluid stream direction. The gas sheet 260 can redirect at least a portion of the sample fluid stream 230 in the redirection area 104. The gas sheet 260 may also break liquid droplets in the sample fluid stream 230, which can promote drying of such droplets. Additionally, the gas sheet 260 can mix a central portion of the sample fluid stream 230 (which can be cooler and wetter than the rest of the sample fluid stream 230) with other portions of the sample fluid stream 230. This may also promote drying of the overall sample fluid stream 230.

The gas sheet 260 can be wider than the sample fluid stream 230. Also, the gas sheet 260 may be curved and have a high velocity. For example, a velocity of the gas sheet 260 may be greater than a velocity of the sample fluid stream 230. For example, the main fluid stream 232 may be flowing with a velocity of about twenty to about sixty miles per hour, and this velocity may be cut in half in the shroud 110 before the sample fluid stream 230 enters the nozzle inlet 122. The gas sheet 260 may have a velocity that is from fifty to two-hundred miles per hour, such as from one-hundred mile per hour to one-hundred and fifty miles per hour. The source of gas for the gas sheet 260 can be heated so that the gas sheet may be at an elevated temperature, such as a temperature above two-hundred and twelve degrees Fahrenheit, such as 250 degrees Fahrenheit.

The sample fluid stream can be transported 335 from the redirection area 104, such as to the materials monitoring apparatus 180. As noted above, the sample fluid stream 230 can be focused, such as using focusing gas 252. The focusing gas 252 in a first section (e.g., the nozzle area 102) can be a lower temperature than focusing gas in a second section (e.g., the redirection area 104 and/or the transport area 106) downstream of the first section. For example, the focusing gas in the second section can be drying gas 270, which can be supplied through the second gas chamber 164 and possibly through subsequent gas chambers (e.g., the third gas chamber 166). This drying gas 270 can focus the sample fluid stream 230 in the redirection area 104 and/or the transport area 106. The drying gas 270 may be heated to an elevated temperature similar to the temperature of the gas sheet 260. Such high temperatures can heat the sample fluid stream 230 and promote drying of droplets in the sample fluid stream 230. The gases discussed above may be air and/or one or more other gases.

The subject matter defined in the appended claims is not necessarily limited to the benefits described herein. A particular implementation of the invention may provide all, some, or none of the benefits described herein. Although operations for the various techniques are described herein in a particular, sequential order for the sake of presentation, it should be understood that this manner of description encompasses rearrangements in the order of operations, unless a particular ordering is required. For example, operations described sequentially may in some cases be rearranged or performed concurrently. Techniques described herein with reference to flowcharts may be used with one or more of the systems described herein and/or with one or more other systems. Moreover, for the sake of simplicity, flowcharts may not show the various ways in which particular techniques can be used in conjunction with other techniques.

In one specific example of the virtual nozzle discussed herein, the diameter of the nozzle inlet might be on the order of one to three inches and the knife edge (the width of the gas sheet outlet 186) might have a slit width opening on the order of 0.001 inch. Consider the following example: 1 inch diameter nozzle; 0.001 inch air knife (gas sheet) opening; 10 lpm (liters per minute) flow through the knife edge slit opening would yield about 190 mph velocity air knife near the outlet. Assuming a stack velocity of 30 mph and sampling flow 1.1 times the stack velocity (slightly super isokinetic), flow through the nozzle would be expected to be about 450 lpm. If a shroud were used to slow the flow by about one third, the nozzle flow would be expected to be about 150 lpm.

In this latter case with the shroud, as the flow approaches the virtual nozzle inlet, the flow could feel the slight increased draw of the larger nozzle flow, which would have a tendency to draw in more fine particles than coarse particles, but the gas sheet could tend to push back preferentially the fine particles thus minimizing any fine particle enrichment that might otherwise take place.

Inside the shroud, the velocity of the main fluid stream could be expected to be on the order of 10 to 20 mph, with the gas sheet in the virtual nozzle pushing in the opposite direction with a velocity approaching almost 200 mph. Under these conditions, it could be that additional focusing of the stack gas may not be needed to produce proper focusing prior to the second air knife that turns the stack gas flow. The diameters, flows and other specific dimensions for specific configurations can be optimized after preliminary tests, such as tests in a wind tunnel.

While the invention has been particularly shown and described with reference to preferred embodiments thereof, it will be understood by those skilled in the art that various changes in form and details may be made therein without departing from the spirit and scope of the invention. For example, one or more of the features discussed herein may be omitted from the probe apparatus and/or the user thereof. For example, the re-entraining 315 of droplets and/or the focusing 320 of the sample fluid stream with the focusing gas 252, as well as associated features of the probe apparatus 100 may be omitted as a result of the focusing and boundary layer effects of the virtual nozzle 182.

I claim:
1. A method comprising:
   receiving a sample fluid stream from a main fluid stream through a nozzle of a probe located at least partially in the main fluid stream, wherein the sample fluid stream flows into the nozzle and a portion of the main fluid stream adjacent to the sample fluid stream flows past the probe without entering the probe, the sample fluid stream flowing downstream within the probe, and a portion of the main fluid stream flowing downstream outside the probe; and
   while receiving the sample fluid stream, directing a gas sheet away from the probe, with the gas sheet flowing upstream against the main fluid stream and separating the sample fluid stream from the main fluid stream.

2. The method of claim 1, wherein gas from the gas sheet forms a layer of gas along an inner surface of the probe that faces the sample fluid stream flowing downstream within the probe.

3. The method of claim 1, wherein gas from the gas sheet forms a layer of gas along an outer surface of the probe that faces the portion of the main fluid stream flowing downstream outside the probe.

4. The method of claim 1, wherein gas from the gas sheet inhibits collection of material from the main fluid stream on one or more outer surfaces of the probe, the one or more outer surfaces facing the portion of the main fluid stream flowing around the probe.

5. The method of claim 1, wherein gas from the gas sheet inhibits collection of material from the main fluid stream on one or more inner surfaces of the probe, the one or more inner surfaces facing the sample fluid stream within the probe.

6. The method of claim 1, wherein gas from the gas sheet inhibits collection of material from the main fluid stream on a leading edge of the probe.

7. The method of claim 1, wherein the main fluid stream includes droplets and wherein the gas sheet sheers and splits droplets from the main fluid stream.

8. The method of claim 1, wherein the gas sheet focuses the sample fluid stream within a central portion of a conduit extending through the nozzle and into the probe.

9. The method of claim 1, wherein the gas sheet passes through an annular opening in the nozzle between an inner surface and an outer surface.

10. The method of claim 9, wherein the inner surface extends farther upstream from a terminus of the outer surface.

11. The method of claim 1, wherein the gas sheet flows from the probe in a direction that is within three degrees of a direction that is directly opposite to a direction of flow of the main fluid stream.

12. The method of claim 1, wherein the gas sheet is an annular gas sheet.

13. The method of claim 1, further comprising passing the sample fluid stream through a shroud before receiving the sample fluid stream through the nozzle of the probe.

14. The method of claim 1, wherein the gas sheet has a velocity of at least 100 miles per hour relative to the probe as the gas sheet leaves an opening in the probe.

15. The method of claim 1, wherein the gas sheet has a velocity of at least 150 miles per hour relative to the probe as the gas sheet leaves an opening in the probe.

16. A probe apparatus comprising:

a nozzle inlet configured to receive a sample fluid stream from a main fluid stream, with the sample fluid stream flowing downstream into the nozzle inlet while a portion of the main fluid stream flows downstream outside the nozzle inlet; and a pressurized gas source connected to a gas sheet outlet, the gas source and the gas sheet outlet being in fluid communication with each other and configured to direct gas from the gas source through the gas sheet outlet, with the probe apparatus being configured such that the gas passing through the gas sheet outlet forms a gas sheet flowing upstream from a leading portion of the nozzle inlet against the flow of the main fluid stream, and with the probe apparatus being configured such that the gas sheet separates the sample fluid stream from the portion of the main fluid stream prior to the sample fluid stream reaching the nozzle inlet.

17. The probe apparatus of claim 16, wherein the gas sheet outlet extends around a perimeter of the nozzle inlet.

18. The probe apparatus of claim 16, wherein the gas sheet outlet is defined by an outer surface and an inner surface, wherein the outer surface faces inwardly toward the inner surface, and wherein the inner surface extends farther upstream relative to the flow of the main fluid stream than the outer surface.

19. The probe apparatus of claim 18, wherein the gas sheet outlet has an opening slit width of less than 0.01 inch.

20. The probe apparatus of claim 18, wherein the gas sheet outlet has an opening slit width of less than 0.005 inch.

21. A method comprising:

receiving a sample fluid stream from a main fluid stream through a nozzle of a probe located at least partially in the main fluid stream, the sample fluid stream traveling into the nozzle and a portion of the main fluid stream adjacent to the sample fluid stream flowing past the probe without entering the probe, the sample fluid stream flowing downstream within the probe, and a portion of the main fluid stream flowing downstream outside the probe; and while receiving the sample fluid stream, directing a gas sheet away from the probe, with the gas sheet flowing upstream against the main fluid stream;

wherein gas from the gas sheet forms a layer of gas along an inner surface of the probe that faces the sample fluid stream flowing downstream with the probe, the layer of gas along the inner surface inhibiting collection of material from the sample fluid stream on the inner surface;

wherein gas from the gas sheet forms a layer of gas along an outer surface of the probe that faces the portion of the main fluid stream flowing downstream outside the probe, the layer of gas along the outer surface inhibiting collection of material from the main fluid stream on the outer surface; and wherein gas from the gas sheet inhibits collection of material from the main fluid stream on a leading edge of the probe.

* * * * *